US 8,513,391 B2

(12) United States Patent
Jones et al.

(10) Patent No.: US 8,513,391 B2
(45) Date of Patent: Aug. 20, 2013

(54) MONOCLONAL ANTIBODIES FOR EBOLA AND MARBURG VIRUSES

(76) Inventors: Steven Jones, Manitoba (CA); Xiangguo Qiu, Manitoba (CA); Heinz Feldmann, Montana, MT (US); Ute Stroeher, Manitoba (CA)

( * ) Notice: Subject to any disclaimer, the term of this patent is extended or adjusted under 35 U.S.C. 154(b) by 245 days.

(21) Appl. No.: 12/864,584

(22) PCT Filed: Jan. 27, 2009

(86) PCT No.: PCT/CA2009/000070
§ 371 (c)(1),
(2), (4) Date: Oct. 26, 2010

(87) PCT Pub. No.: WO2009/094755
PCT Pub. Date: Aug. 6, 2009

(65) Prior Publication Data
US 2012/0283414 A1    Nov. 8, 2012

Related U.S. Application Data

(60) Provisional application No. 61/025,491, filed on Feb. 1, 2008.

(51) Int. Cl.
*C07K 16/08*    (2006.01)
*A61K 39/40*    (2006.01)
*C12N 15/09*    (2006.01)

(52) U.S. Cl.
USPC ............ 530/388.3; 530/367.1; 530/387.3; 530/388.1; 424/149.1; 424/133.1; 424/130.1; 435/69.1; 435/69.6; 435/70.1

(58) Field of Classification Search
None
See application file for complete search history.

(56) References Cited

U.S. PATENT DOCUMENTS

| 6,020,153 | A  | * | 2/2000  | Hardman et al. | 435/69.1 |
| 6,120,767 | A  | * | 9/2000  | Robinson et al. | 424/133.1 |
| 6,204,023 | B1 | * | 3/2001  | Robinson et al. | 435/71.3 |
| 6,461,824 | B1 | * | 10/2002 | Better et al. | 435/7.23 |

FOREIGN PATENT DOCUMENTS

WO    WO 2004/018649    3/2004

OTHER PUBLICATIONS

Paul, Fundamental Immunology, 3rd Edition, 1993, pp. 292-295.*
Takada, A. et al., "Protective Efficacy of Neutralizing Antibodies Against Ebola Virus Infection", Vaccine, 2007, vol. 25, pp. 993-999, ISSN: 0264-410X.
Shahhosseini, S. et al., "Production and characterization of monoclonal antibodies against different epitopes of Ebola virus antigens", Journal of Virological Methods, 2007, vol. 143, pp. 29-37, ISSN: 0166-0934.

* cited by examiner

*Primary Examiner* — Sheela J Huff
*Assistant Examiner* — Jessica H Roark
(74) *Attorney, Agent, or Firm* — Michael R Williams; Ade & Company Inc

(57) ABSTRACT

Described herein are a number of Ebola and Marburg monoclonal antibodies.

4 Claims, 4 Drawing Sheets

Kaplan-Meier Survival Curve of Mice infected with MA-ZEBOV and Treated with MAbs 1 day after infection

Fig. 1

Weight Changes of GPA-Ebola infected Guinea Pigs Treated with MAbs

Fig. 2

Weight Changes of GPA-Ebola infected Guinea Pigs Treated with MAbs

Fig. 3

SEQUENCE LISTING

<160> NUMBER OF SEQ ID NOS: 21

<210> SEQ ID NO 1
<211> LENGTH: 373
<212> TYPE: DNA
<213> ORGANISM: mouse

<400> SEQUENCE: 1

```
tgggcagag cttgtgaagc caggggcctc agtcaagttg tcctgcacag cttctggctt      60
caacattaaa gacacctata tacattgggt gaaacagggg cctgaacagg gcctggagtg     120
gattggaagg attgatcctg cgaatggtaa tactaaatat gacccgaagt tccagggcaa     180
ggccactatc acagcagaca catcctccaa tacagcctac ctgcagctca gcggcctgac     240
atctgaggac actgccgtct attactgtgc tagggagtcg aggatatcta ctatgcttac     300
gacggggtac tttgactact ggggccaagg caccactctc acagtctcct cagccaaaac     360
aacagcccca tcg                                                        373
```

<210> SEQ ID NO 2
<211> LENGTH: 303
<212> TYPE: DNA
<213> ORGANISM: mouse

<400> SEQUENCE: 2

```
gcaatcatgt ctgcatctcc aggggagaag gtcaccatga cctgcagtgc cagctcaagt      60
gtaagttaca tgtactggta ccagcagaag ccaggatcct cccccagact cctgatttat     120
gacacatcca acctggcttc tggagtccct gttcgcttca gtggcagtgg gtctgggacc     180
tcttactctc tcacaatcag ccgaatggag gctgaagatg ctgccactta ttactgccag     240
cagtggagta gttacccgta cacgttcgga ggggggacca agctggaaat aaaacgggct     300
gat                                                                   303
```

<210> SEQ ID NO 3
<211> LENGTH: 364
<212> TYPE: DNA

<213> ORGANISM: mouse

<400> SEQUENCE: 3

| tggaggaggc | ttgatgcaac | ctggaggatc | catgaaactc | tcctgtgttg | cctcaggatt | 60 |
| cactttcagt | aactactgga | tgaactgggt | ccgccagtct | ccagagaagg | ggcttgagtg | 120 |
| ggttgctgaa | attagattga | aatctaataa | ttatgcaaca | cattatgcgg | agtctgtgaa | 180 |
| agggaggttc | accatttcaa | gagatgattc | caaaaggagt | gtctacctgc | aaatgaatac | 240 |
| cttaagagct | gaagacactg | gcatttatta | ctgtacccgg | gggaatggta | actacagggc | 300 |
| tatggactac | tggggtcaag | gaacctcagt | caccgtctcc | tcagccaaaa | caacaccccc | 360 |
| atca | | | | | | 364 |

<210> SEQ ID NO 4
<211> LENGTH: 306
<212> TYPE: DNA
<213> ORGANISM: mouse

<400> SEQUENCE: 4

| gcctccctat | ctgtatctgt | gggagaaact | gtctccatca | catgtcgagc | aagtgagaat | 60 |
| atttacagta | gtttagcatg | gtatcagcag | aaacagggaa | aatctcctca | gctcctggtc | 120 |
| tattctgcaa | caatcttagc | agatggtgtg | ccatcaaggt | tcagtggcag | tggatcaggc | 180 |
| actcagtatt | ccctcaagat | caacagcctg | cagtctgaag | attttgggac | ttattactgt | 240 |
| caacattttt | ggggtactcc | gtacacgttc | ggaggggga | ccaagctgga | aataaaacgg | 300 |
| gctgat | | | | | | 306 |

<210> SEQ ID NO 5
<211> LENGTH: 358
<212> TYPE: DNA
<213> ORGANISM: mouse

<400> SEQUENCE: 5

| tggacctgag | ctggagatgc | ctggcgcttc | agtgaagata | tcctgcaagg | cttctggttc | 60 |
| ctcattcact | ggcttcagta | tgaactgggt | gaagcagagc | aatggaaaga | gccttgagtg | 120 |
| gattggaaat | attgatactt | attatggtgg | tactacctac | aaccagaaat | tcaagggcaa | 180 |
| ggccacattg | actgtggaca | aatcctccag | cacagcctac | atgcagctca | gagcctgac | 240 |
| atctgaggac | tctgcagtct | attactgtgc | aagatcggcc | tactacggta | gtacttttgc | 300 |
| ttactggggc | caagggactc | tggtcactgt | ctctgcagcc | aaaacaacag | ccccatcg | 358 |

<210> SEQ ID NO 6
<211> LENGTH: 306
<212> TYPE: DNA
<213> ORGANISM: mouse

<400> SEQUENCE: 6

| gcctccctat | ctgcatctgt | gggagaaact | gtcaccatca | catgtcgagc | aagtgagaat | 60 |
| atttacagtt | atttagcatg | gtatcagcag | aaacagggaa | aatctcctca | gctcctggtc | 120 |
| tataatgcca | aaaccttaat | agagggtgtg | ccatcaaggt | tcagtggcag | tggatcaggc | 180 |
| acacagtttt | ctctgaagat | caacagcctg | cagcctgaag | attttgggag | ttatttctgt | 240 |
| caacatcatt | ttggtactcc | attcacattc | ggctcgggga | cagagttgga | aataaaacgg | 300 |
| gctgat | | | | | | 306 |

<210> SEQ ID NO 7

```
<211> LENGTH: 340
<212> TYPE: DNA
<213> ORGANISM: mouse

<400> SEQUENCE: 7
gggacctggc ctggtgagac cttctcagtc tctgtccctc acctgcactg tcactggcta      60
ctcaatcacc agtgattatg cctggaactg gatccggcag tttccaggaa acaaactgga     120
gtggctgggc tatataacca acactggtag cactggcttc aacccatctc tcaaaagtcg     180
aatctctatc actcgagaca catccaagaa ccagttcttc ctgcagttga tttctgtgac     240
tactgaggac acagccacat atcactgtgc aaggggcctt gcttactggg gccaagggac     300
tctggtcact gtctctgcag ccaaaacaac agccccatcg                           340

<210> SEQ ID NO 8
<211> LENGTH: 321
<212> TYPE: DNA
<213> ORGANISM: mouse

<400> SEQUENCE: 8
ctcactttgt cggttaccat tggacaacca gcctccatct cttgcaagtc aagtcagagc      60
ctcttagata gtgatggaaa gacatatctg aattggttgt tacagaggcc aggccagtct     120
ccaaagcgcc taatctatct ggtgtctaaa ctggactctg gagtcactga caggttcact     180
ggcagtggat cagggacaga tttcacactg aaaatcagca gagtggaggc tgaggatttg     240
ggagtttatt attgttggca aggtacacac tctccattca cgttcggctc ggggacaaag     300
ttggaaataa aacgggctga t                                               321

<210> SEQ ID NO 9
<211> LENGTH: 370
<212> TYPE: DNA
<213> ORGANISM: mouse

<400> SEQUENCE: 9
tgggggaggc ttagtgaagc ctggagggtc cctgaaactc tcctgtgcag cctctggatc      60
cgctttcagt agatatgaca tgtcttgggt tcgccagact ccggagaaga ggctggagtg     120
ggtcgcatac attagtcgtg gtggtggttt catctactat ccagacactg tgaagggccg     180
attcaccatc tccagagaca atgccaagaa caccctgtac ctgcaaatga gcagtctgaa     240
gtctgacgac acagccatgt attactgtgc aagacacgtt tactacggta gtagccccct     300
ctatgctatg gactactggg gtcaaggaac ctcagtcacc gtctcctcag ccaaaacaac     360
agccccatcg                                                            370

<210> SEQ ID NO 10
<211> LENGTH: 324
<212> TYPE: DNA
<213> ORGANISM: mouse

<400> SEQUENCE: 10
tcagcctctt tctccctggg agcctcagca aaactcacgt gcaccttgag tagtcagcac      60
agtacgttca ccattgaatg gtatcagcaa cagccactca gcctcctaa gtatgtgatg     120 gagcttaaga aagatggaag ccacagtaca ggtgatggga ttcctgatcg cttctctgga     180
tccagctctg gtgctgatcg ctaccttagc atttccaaca tccagcctga agatgaagca     240
atatacatct gtggtgtggg tgatacaatt aatgaacaat tgtgtatgt tttcggcggt     300 ggaaccaagg tcactgtcct aggt                                           324
```

<210> SEQ ID NO 11
<211> LENGTH: 358
<212> TYPE: DNA
<213> ORGANISM: mouse

<400> SEQUENCE: 11
tggggcagag cttgtgaagc caggggcctc agtcaagttg tcctgcacag cttctggctt      60
caacattaaa gacacctata tgcactgggt gaaggagagg cctgacaagg gcctggagtg     120
gattggaagg attgatccag cgaatggtaa tactaaatgt gactcgaggt ttcagggcaa     180
ggccactata acagcagaca catcctccaa cacagcctac ctgcagctca gcagcctgac     240
atctgaggac actgccgtct attactgtgc tagaaggatc tactttggta agggctttga     300
cttttggggc caaggcacca ctctcacagt ctcctcagcc aaaacaacag ccccatcg      358

<210> SEQ ID NO 12
<211> LENGTH: 324
<212> TYPE: DNA
<213> ORGANISM: mouse

<400> SEQUENCE: 12 tcctcccctga gtgtgtcagc aggagagaag gtcactatga gctgcaagtc cagtcagagt      60
ctgtttaaca gtgagatca aaagaactac ttggcctggt accagcagaa accagggcag     120
cctcctaaac tgttgatcta cggggcatcc actagggaat ctggggtccc tgatcgcttc     180
acaggcagtg gatctggaac cgatttcact cttaccatca gcagtgtgca ggctgaagac     240
ctggcagttt attactgtca gaatgatcaa ttttatcctc ccacgttcgg tgatgggacc     300
aagctggacc tgaaacgggc tgat                                            324

<210> SEQ ID NO 13
<211> LENGTH: 367
<212> TYPE: DNA
<213> ORGANISM: mouse

<400> SEQUENCE: 13 tggaggggc ttggtacagc ctgggggttc tctgagactc tcctgtgcaa cttctggctt      60
cacctttact gatcactaca tgggctgggt ccgccagcct ccaggaaagg cacttgagtg     120
gttggctttt gttagataca aagctaaggg ttacacaaca gagtacactg catctgtgaa     180
gggtcggttc accatctcca gagataattc ccaaagcatc ctctatcttc aaatgaacac     240
cctgagaact gaggacagtg ccacttatta ctgtgcaaga gatagagggg gttacgtggg     300
agctatggac tactggggtc aaggaacctc agtcaccgtc tcctcagcca aaacgacacc     360
cccatct                                                               367

<210> SEQ ID NO 14
<211> LENGTH: 321
<212> TYPE: DNA
<213> ORGANISM: mouse

<400> SEQUENCE: 14 ctctcccctgc ctgtcagtct tggagatcaa gcctccatct cttgcagatc tagtcagagc      60
cttgtacaca ggaatggaaa cacctatttc cattggtacc tgcagaagcc aggccagtct     120
ccaaaactcc tgatctacaa agtttccaac cgattttctg gggtcccaga caggttcagt     180
ggcagtggat cagggacaga tttcacactc aagatcagca gagtggaggc tgaggatctg     240
ggagtttatt tctgctctca aagtacacat gttccgtaca ctttcggagg ggggaccaag     300

-continued

| ctggaaataa aacgggctga t | 321 |

<210> SEQ ID NO 15
<211> LENGTH: 352
<212> TYPE: DNA
<213> ORGANISM: mouse

<400> SEQUENCE: 15

| tggggcagag cttgtgaggt caggggcctc agtcaagttg tcctgcacat cttctggctt | 60 |
| caacattaaa gactactttc tacactgggt gaaacagagg cctgaacagg gcctggagtg | 120 |
| gattggatgg attgatcctg agaatggtga tactgaatat gccccgaagt tccaggacaa | 180 |
| ggccactatg actgcagaca catcctccaa cacagcctac ctgcacctca gcagcctgac | 240 |
| atctgaggac actggcgtct attactgtaa tgcagatggt aactacggga gaaactactg | 300 |
| gggccaaggc accactctca ccgtctcctc agccaaaaca acagccccat cg | 352 |

<210> SEQ ID NO 16
<211> LENGTH: 324
<212> TYPE: DNA
<213> ORGANISM: mouse

<400> SEQUENCE: 16

| ctctccctgc tgtcagtct tggagatcaa gcctccatct cttgcagatc tagtcagagc | 60 |
| cttgtacaca gtaatggaaa caccttttta cattggtacc tgcagaagcc aggccagtct | 120 |
| ccaaagctcc tgatctacag agtttccaac cgatttctg gggtcccaga caggttcagt | 180 |
| ggcagtggat cagggacaga tttcacactc aagatcagca gagtggaggc tgaggatctg | 240 |
| ggagtttatt tctgctctca agtacacat gttcctccgt acacgttcgg agggggacc | 300 |
| aagctggaaa taaaacgggc tgat | 324 |

<210> SEQ ID NO 17
<211> LENGTH: 15
<212> TYPE: PRT
<213> ORGANISM: mouse

<400> SEQUENCE: 17

Ser Asn Thr Thr Gly Lys Leu Ile Trp Lys Val Asn Pro Glu Ile
1               5                   10                  15

<210> SEQ ID NO 18
<211> LENGTH: 15
<212> TYPE: PRT
<213> ORGANISM: mouse

<400> SEQUENCE: 18

Arg Glu Ala Ile Val Asn Ala Gln Pro Lys Cys Asn Pro Asn Leu
1               5                   10                  15

<210> SEQ ID NO 19
<211> LENGTH: 15
<212> TYPE: PRT
<213> ORGANISM: mouse

<400> SEQUENCE: 19

Arg Glu Ala Ile Val Asn Ala Gln Pro Lys Cys Asn Pro Asn Leu
1               5                   10                  15

<210> SEQ ID NO 20
<211> LENGTH: 15
<212> TYPE: PRT
<213> ORGANISM: mouse

```
<400> SEQUENCE: 20

Asp Pro Gly Thr Asn Thr Thr Glu Asp His Lys Ile Met Ala
1               5                   10                  15

<210> SEQ ID NO 21
<211> LENGTH: 15
<212> TYPE: PRT
<213> ORGANISM: mouse

<400> SEQUENCE: 21

Ala Thr Gln Val Glu Gln His His Arg Arg Thr Asp Asn Asp Ser
1               5                   10                  15
```

MONOCLONAL ANTIBODIES FOR EBOLA AND MARBURG VIRUSES

PRIOR APPLICATION INFORMATION

The instant application claims the benefit of U.S. Provisional Patent Application 61/025,491, filed Feb. 1, 2008.

BACKGROUND OF THE INVENTION

Ebola and Marburg viruses are highly pathogenic and virulent viruses causing rapidly fatal haemorrhagic fever in humans.

SUMMARY OF THE INVENTION

According to a first aspect of the invention, there is provided a monoclonal antibody comprising an amino acid sequence deduced from 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14), 10C8-light (SEQ ID No. 16), 1H3-heavy (SEQ ID No. 1); 2G4-heavy (SEQ ID No. 3); 4G7-heavy (SEQ ID No. 5); 5D2-heavy (SEQ ID No. 7); 5E6-heavy (SEQ ID No. 9), 7C9-heavy (SEQ ID No. 11), 7G4-heavy (SEQ ID No. 13) and 10C8-heavy (SEQ ID No. 15).

According to a second aspect of the invention, there is provided a method of preparing a chimeric antibody comprising:

providing an expression vector comprising a nucleic acid molecule encoding a constant region domain of a human light chain or heavy chain genetically linked to a nucleic acid encoding a light chain variable region selected from the group consisting of 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14) and 10C8-light (SEQ ID No. 16) or a heavy chain variable region selected from the group consisting of 1H3-heavy (SEQ ID No. 1); 2G4-heavy (SEQ ID No. 3); 4G7-heavy (SEQ ID No. 5); 5D2-heavy (SEQ ID No. 7), 5E6-heavy (SEQ ID No. 9), 7C9-heavy (SEQ ID No. 11), 7G4-heavy (SEQ ID No. 13) and 10C8-heavy (SEQ ID No. 15);

expressing the expression vector in a suitable host; and recovering the chimeric antibody from said host.

According to a third aspect of the invention, there is provided a method of preparing a recombinant antibodies comprising:

providing a nucleotide sequence selected from the group consisting of 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-fight (SEQ ID No. 12); 7G4-light (SEQ ID No. 14), 10C8-light (SEQ ID No. 16), 1H3-heavy (SEQ ID No. 1); 2G4-heavy (SEQ ID No. 3); 4G7-heavy (SEQ ID No. 5); 5D2-heavy (SEQ ID No. 7), 5E6-heavy (SEQ ID No. 9), 7C9-heavy (SEQ ID No. 11), 7G4-heavy (SEQ ID No. 13) and 10C8-heavy (SEQ ID No. 15);

modifying said nucleic acid sequence such that at least one but fewer than about 30 of the amino acid residues encoded by said nucleic acid sequence has been changed or deleted without disrupting antigen binding of said peptide; and expressing and recovering said modified nucleotide sequence.

BRIEF DESCRIPTION OF THE DRAWINGS

FIG. 1. Kaplan-Meier survival curve of mice infected with MA-ZEBOV and treated with MAbs 1 day after infection. Survival curve of MA-Ebola virus-infected mice treated with 100 μg of MAbs. Mice were intraperitoneally treated with 100 μg of each MAb on day 1. Control mice were given equal volumes of PBS.

FIG. 2. Weight changes of GPA-Ebola infected guinea pigs treated with MAbs. Weight changes of virus-infected guinea pigs treated with cocktail of MAbs. Guinea pigs were intraperitoneally treated with either 5D2, 5E6, 7C9, 7G4 or 10C8 (3 mg/treatment) on day 1 and 4G7+1H3+2G4 [(2 mg+1 mg+1 mg)/treatment] on day 2. Control guinea pig were given equal volume of PBS. The results are shown as the means and standard deviations of 6 guinea pigs.

FIG. 3. Weight changes of GPA-Ebola infected guinea pigs treated with MAbs. Weight changes of virus-infected guinea pigs treated with cocktail of MAbs. Guinea pigs were intraperitoneally treated with either 5D2, 5E6, 7C9, 7G4 or 10C8 (3 mg/treatment) on day 1 and 4G7+1H3+2G4 [(2 mg+1 mg+1 mg)/treatment] on day 2. Control guinea pig were given equal volume of PBS. The results are shown as the group weight of 6 guinea pigs.

DESCRIPTION OF THE PREFERRED EMBODIMENTS

Figure 4:
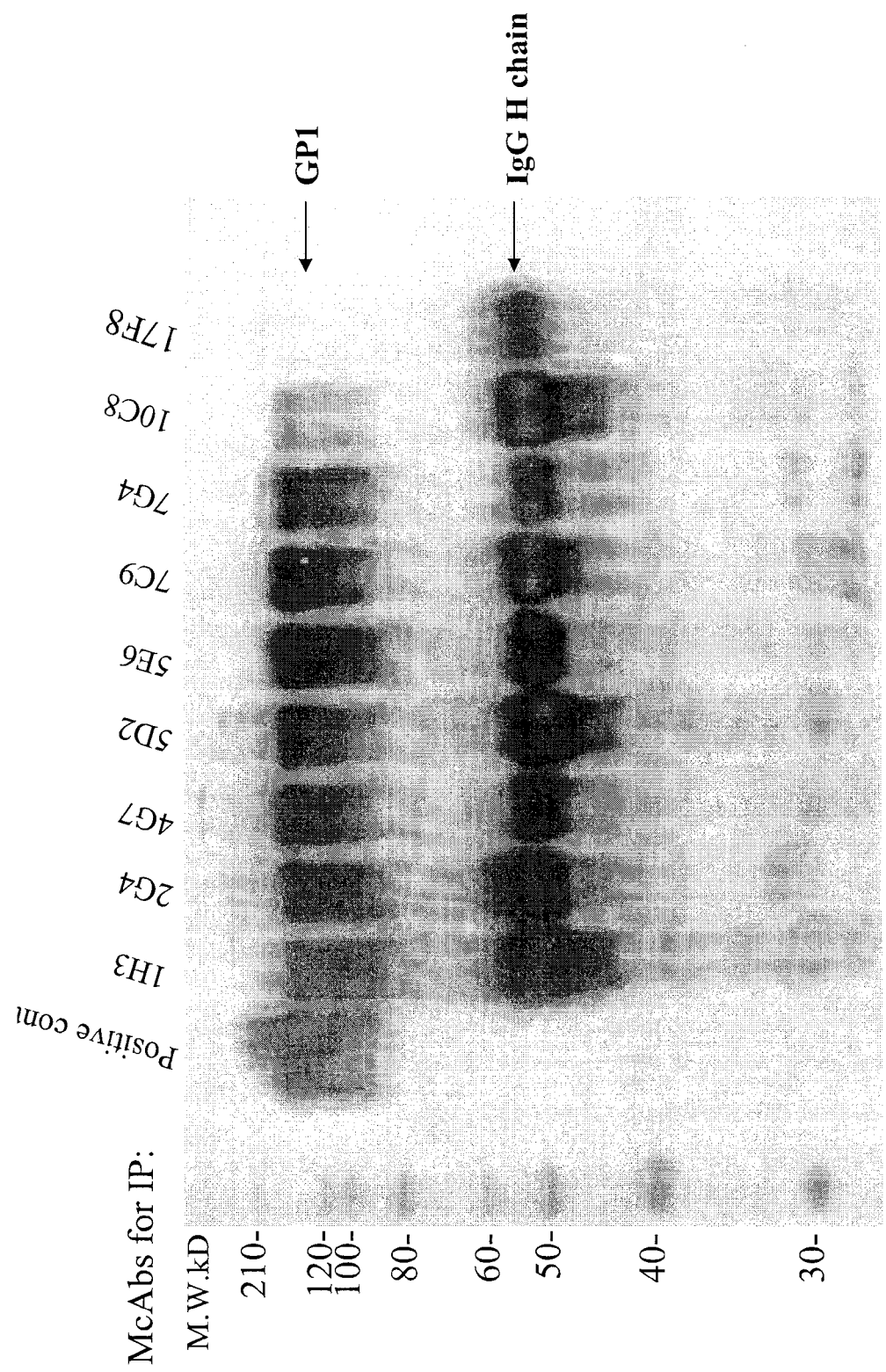
FIG. 4. Immunoprecipitation. 293T cells were transfected with pCAGGS-ZEbovGP1,2 by using Fugene 6. After 48 hrs, cells were collected and washed 2× with cold PBS before being lysed with 2× RIPA buffer. After clarifying the cell lysate, 100 μg protein was added to each McAb (5 μg) coupled protein A+G beads. The IP samples were run 10% SDS-PAGE and transferred to Hybond-P membrane. The blot was probed with mouse ant-EBOV-GP1.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

DEFINITIONS

As used herein, "neutralizing antibody" refers to an antibody, for example, a monoclonal antibody, capable of disrupting a formed viral particle or inhibiting formation of a viral particle or prevention of binding to or infection of mammalian cells by a viral particle.

As used herein, "diagnostic antibody" or "detection antibody" or "detecting antibody" refers to an antibody, for example, a monoclonal antibody, capable of detecting the presence of an antigenic target within a sample. As will be appreciated by one of skill in the art, such diagnostic antibodies preferably have high specificity for their antigenic target.

As used herein, "humanized antibodies" refer to antibodies with reduced immunogenicity in humans.

As used herein, "chimeric antibodies" refer to antibodies with reduced immunogenicity in humans built by genetically linking a non-human Variable region to human constant domains.

Described herein are a number of Ebola and Marburg monoclonal antibodies. Specifically, antigens were developed using a live replicating vector vesicular stomatitis virus described in PCT Application PCT/CA03/001125.

The VSV based vaccine delivery system was used to develop monoclonal antibodies in mice.

Specifically, described herein are monoclonal antibodies 1H3, 2G4, 4G7, 5D2, 5E6, 7C9, 7G4 and 10C8. As discussed below, 1H3 comprises 1H3-heavy chain (SEQ ID No. 1) and 1H3-light chain (SEQ ID No. 2); 2G4 comprises 2G4-heavy chain (SEQ ID No. 3) and 2G4-light chain (SEQ ID No. 4); 4G7 comprises 4G7-heavy chain (SEQ ID No. 5) and 4G7-light chain (SEQ ID No. 6); 5D2 comprises 5D2-heavy chain (SEQ ID No. 7) and 5D2-light chain (SEQ ID No. 8); 5E6 comprises 5E6-heavy chain (SEQ ID No. 9) and 5E6-light chain (SEQ ID No. 10); 7C9 comprises 7C9-heavy chain (SEQ ID No. 11) and 7C9-light chain (SEQ ID No. 12); 7G4 comprises 7G4-heavy chain (SEQ ID No. 13) and 7G4-light chain (SEQ ID No. 14); and 10C8 comprises 10C8-light chain (SEQ ID No. 16) and 10C8-heavy chain (SEQ ID No. 15).

These antibodies also appear to have high affinity and avidity to Ebola glycoproteins, which means that they could be used as highly sensitive diagnostic tools.

For example, as shown in FIG. 1, mice infected with MA-ZEBOV and subsequently treated with the monoclonal antibodies described above showed increased survival compared to mice treated with PBS. Results are summarized in Tables 1 and 2.

FIGS. 2 and 3 show weight changes in guinea pigs treated with the monoclonal antibodies or mixtures thereof post infection. As can be seen, guinea pigs treated with the monoclonal antibodies showed consistent weight while those treated with PBS showed significant weight loss. Results are summarized in Table 3.

The nucleotide sequences of the heavy and light chains of 1H3, 2G4, 4G7, 5D2, 5E6, 7C9, 7G4 and 10C8 follow. As will be appreciated by one of skill in the art, the amino acid sequences of these antibodies can easily be deduced from the nucleotide sequences. Accordingly, in some embodiments, the invention is directed to amino acid sequences deduced from 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14), 10C8-light (SEQ ID No. 16), 1H3-heavy (SEQ ID No. 1); 2G4-heavy (SEQ ID No. 3); 4G7-heavy (SEQ ID No. 5); 5D2-heavy (SEQ ID No. 7), 5E6-heavy (SEQ ID No. 9), 7C9-heavy (SEQ ID No. 11), 7G4-heavy (SEQ ID No. 13) and 10C8-heavy (SEQ ID No. 15).

```
mAb 1H3 heavy chain sequence: 373 bp
                                        (SEQ ID No. 1)
TGGGGCAGAGCTTGTGAAGCCAGGGGCCTCAGTCAAGTTGTCCTGCACA

GCTTCTGGCTTCAACATTAAAGACACCTATATACATTGGGTGAAACAGG

GGCCTGAACAGGGCCTGGAGTGGATTGGAAGGATTGATCCTGCGAATGG

TAATACTAAATATGACCCGAAGTTCCAGGGCAAGGCCACTATCACAGCA

GACACATCCTCCAATACAGCCTACCTGCAGCTCAGCGGCCTGACATCTG

AGGACACTGCCGTCTATTACTGTGCTAGGGAGTCGAGGATATCTACTAT

GCTTACGACGGGGTACTTTGACTACTGGGGCCAAGGCACCACTCTCACA

GTCTCCTCAGCCAAAACAACAGCCCCATCG mAb 1H3 light chain sequence: 303 bp
                                        (SEQ ID No. 2)
GCAATCATGTCTGCATCTCCAGGGGAGAAGGTCACCATGACCTGCAGTG

CCAGCTCAAGTGTAAGTTACATGTACTGGTACCAGCAGAAGCCAGGATC

CTCCCCCAGACTCCTGATTTATGACACATCCAACCTGGCTTCTGGAGTC

CCTGTTCGCTTCAGTGGCAGTGGGTCTGGGACCTCTTACTCTCTCACAA

TCAGCCGAATGGAGGCTGAAGATGCTGCCACTTATTACTGCCAGCAGTG

GAGTAGTTACCCGTACACGTTCGGAGGGGGGACCAAGCTGGAAATAAAA

CGGGCTGAT mAb 2G4 heavy chain sequence: 364 bp
                                        (SEQ ID No. 3)
TGGGAGGAGGCTTGATGCAACCTGGAGGATCCATGAAACTCTCCTGTGTT

GCCTCAGGATTCACTTTCAGTAACTACTGGATGAACTGGGTCCGCCAGT

CTCCAGAGAAGGGGCTTGAGTGGGTTGCTGAAATTAGATTGAAATCTAA

TAATTATGCAACACATTATGCGGAGTCTGTGAAAGGGAGGTTCACCATT

TCAAGAGATGATTCCAAAAGGAGTGTCTACCTGCAAATGAATACCTTAA

GAGCTGAAGACACTGGCATTTATTACTGTACCCGGGGGAATGGTAACTA

CAGGGCTATGGACTACTGGGGTCAAGGAACCTCAGTCACCGTCTCCTCA

GCCAAAACAACACCCCCATCA mAb 2G4 light chain sequence: 306 bp
                                        (SEQ ID No. 4)
GCCTCCCTATCTGTATCTGTGGGAGAAACTGTCTCCATCACATGTCGAG

CAAGTGAGAATATTTACAGTAGTTTAGCATGGTATCAGCAGAAACAGGG

AAAATCTCCTCAGCTCCTGGTCTATTCTGCAACAATCTTAGCAGATGGT

GTGCCATCAAGGTTCAGTGGCAGTGGATCAGGCACTCAGTATTCCCTCA

AGATCAACAGCCTGCAGTCTGAAGATTTTGGGACTTATTACTGTCAACA

TTTTTGGGGTACTCCGTACACGTTCGGAGGGGGGACCAAGCTGGAAATA

AAACGGGCTGAT mAb 4G7 heavy chain sequence: 358 bp
                                        (SEQ ID No. 5)
TGGACCTGAGCTGGAGATGCCTGGCGCTTCAGTGAAGATATCCTGCAAG

GCTTCTGGTTCCTCATTCACTGGCTTCAGTATGAACTGGGTGAAGCAGA

GCAATGGAAAGAGCCTTGAGTGGATTGGAAATATTGATACTTATTATGG

TGGTACTACCTACAACCAGAAATTCAAGGGCAAGGCCACATTGACTGTG

GACAAATCCTCCAGCACAGCCTACATGCAGCTCAAGAGCCTGACATCTG

AGGACTCTGCAGTCTATTACTGTGCAAGATCGGCCTACTACGGTAGTAC

TTTTGCTTACTGGGGCCAAGGGACTCTGGTCACTGTCTCTGCAGCCAAA

ACAACAGCCCCATCG mAb 4G7 light chain sequence: 306 bp
                                        (SEQ ID No. 6)
GCCTCCCTATCTGCATCTGTGGGAGAAACTGTCACCATCACATGTCGAG

CAAGTGAGAATATTTACAGTTATTTAGCATGGTATCAGCAGAAACAGGG

AAAATCTCCTCAGCTCCTGGTCTATAATGCCAAAACCTTAATAGAGGGT

GTGCCATCAAGGTTCAGTGGCAGTGGATCAGGCACACAGTTTTCTCTGA

AGATCAACAGCCTGCAGCCTGAAGATTTTGGGAGTTATTTCTGTCAACA

TCATTTTGGTACTCCATTCACATTCGGCTCGGGGACAGAGTTGGAAATA

AAACGGGCTGAT mAb 5D2 heavy chain sequence: 340 bp
                                        (SEQ ID No. 7)
GGGACCTGGCCTGGTGAGACCTTCTCAGTCTCTGTCCCTCACCTGCACT

GTCACTGGCTACTCAATCACCAGTGATTATGCCTGGAACTGGATCCGGC
```

AGTTTCCAGGAAACAAACTGGAGTGGCTGGGCTATATAACCAACACTGG
TAGCACTGGCTTCAACCCATCTCTCAAAAGTCGAATCTCTATCACTCGA
GACACATCCAAGAACCAGTTCTTCCTGCAGTTGATTTCTGTGACTACTG
AGGACACAGCCACATATCACTGTGCAAGGGGCCTTGCTTACTGGGGCCA
AGGGACTCTGGTCACTGTCTCTGCAGCCAAAACAACAGCCCCATCG mAb 5D2 light chain sequence: 321 bp
(SEQ ID No. 8)
CTCACTTTGTCGGTTACCATTGGACAACCAGCCTCCATCTCTTGCAAGT
CAAGTCAGAGCCTCTTAGATAGTGATGGAAAGACATATCTGAATTGGTT
GTTACAGAGGCCAGGCCAGTCTCCAAAGCGCCTAATCTATCTGGTGTCT
AAACTGGACTCTGGAGTCACTGACAGGTTCACTGGCAGTGGATCAGGGA
CAGATTTCACACTGAAAATCAGCAGAGTGGAGGCTGAGGATTTGGGAGT
TTATTATTGTTGGCAAGGTACACACTCTCCATTCACGTTCGGCTCGGGG
ACAAAGTTGGAAATAAAACGGGCTGAT mAb 5E6 heavy chain sequence: 370 bp
(SEQ ID No. 9)
TGGGGGAGGCTTAGTGAAGCCTGGAGGGTCCCTGAAACTCTCCTGTGCA
GCCTCTGGATCCGCTTTCAGTAGATATGACATGTCTTGGGTTCGCCAGA
CTCCGGAGAAGAGGCTGGAGTGGGTCGCATACATTAGTCGTGGTGGTGG
TTTCATCTACTATCCAGACACTGTGAAGGGCCGATTCACCATCTCCAGA
GACAATGCCAAGAACACCCTGTACCTGCAAATGAGCAGTCTGAAGTCTG
ACGACACAGCCATGTATTACTGTGCAAGACACGTTTACTACGGTAGTAG
CCCCCTCTATGCTATGGACTACTGGGGTCAAGGAACCTCAGTCACCGTC
TCCTCAGCCAAAACAACAGCCCCATCG mAb 5E6 light chain sequence: 324 bp
(SEQ ID No. 10)
TCAGCCTCTTTCTCCCTGGGAGCCTCAGCAAAACTCACGTGCACCTTGA
GTAGTCAGCACAGTACGTTCACCATTGAATGGTATCAGCAACAGCCACT
CAAGCCTCCTAAGTATGTGATGGAGCTTAAGAAAGATGGAAGCCACAGT
ACAGGTGATGGGATTCCTGATCGCTTCTCTGGATCCAGCTCTGGTGCTG
ATCGCTACCTTAGCATTTCCAACATCCAGCCTGAAGATGAAGCAATATA
CATCTGTGGTGGGTGATACAATTAATGAACAATTTGTGTATGTTTTC
GGCGGTGGAACCAAGGTCACTGTCCTAGGT mAb 7C9 heavy chain sequence: 358 bp
(SEQ ID No. 11)
TGGGGCAGAGCTTGTGAAGCCAGGGGCCTCAGTCAAGTTGTCCTGCACA
GCTTCTGGCTTCAACATTAAAGACACCTATATGCACTGGGTGAAGGAGA
GGCCTGACAAGGGCCTGGAGTGGATTGGAAGGATTGATCCAGCGAATGG
TAATACTAAATGTGACTCGAGGTTTCAGGGCAAGGCCACTATAACAGCA
GACACATCCTCCAACACAGCCTACCTGCAGCTCAGCAGCCTGACATCTG
AGGACACTGCCGTCTATTACTGTGCTAGAAGGATCTACTTTGGTAAGGG
CTTTGACTTTTGGGGCCAAGGCACCACTCTCACAGTCTCCTCAGCCAAA
ACAACAGCCCCATCG mAb 7C9 light chain sequence: 324 bp
(SEQ ID No. 12)
TCCTCCCTGAGTGTGTCAGCAGGAGAGAAGGTCACTATGAGCTGCAAGT
CCAGTCAGAGTCTGTTTAACAGTGGAGATCAAAAGAACTACTTGGCCTG
GTACCAGCAGAAACCAGGGCAGCCTCCTAAACTGTTGATCTACGGGGCA
TCCACTAGGGAATCTGGGGTCCCTGATCGCTTCACAGGCAGTGGATCTG
GAACCGATTTCACTCTTACCATCAGCAGTGTGCAGGCTGAAGACCTGGC
AGTTTATTACTGTCAGAATGATCAATTTTATCCTCCCACGTTCGGTGAT
GGGACCAAGCTGGACCTGAAACGGGCTGAT mAb 7G4 heavy chain sequence: 367 bp
(SEQ ID No. 13)
TGGAGGGGCTTGGTACAGCCTGGGGGTTCTCTGAGACTCTCCTGTGCA
ACTTCTGGCTTCACCTTTACTGATCACTACATGGGCTGGGTCCGCCAGC
CTCCAGGAAAGGCACTTGAGTGGTTGGCTTTTGTTAGATACAAAGCTAA
GGGTTACACAACAGAGTACACTGCATCTGTGAAGGGTCGGTTCACCATC
TCCAGAGATAATTCCCAAAGCATCCTCTATCTTCAAATGAACACCCTGA
GAACTGAGGACAGTGCCACTTATTACTGTGCAAGAGATAGAGGGGGTTA
CGTGGGAGCTATGGACTACTGGGGTCAAGGAACCTCAGTCACCGTCTCC
TCAGCCAAAACGACACCCCCATCT mAb 7G4 light chain sequence: 321 bp
(SEQ ID No. 14)
CTCTCCCTGCCTGTCAGTCTTGGAGATCAAGCCTCCATCTCTTGCAGAT
CTAGTCAGAGCCTTGTACACAGGAATGGAAACACCTATTTCCATTGGTA
CCTGCAGAAGCCAGGCCAGTCTCCAAAACTCCTGATCTACAAAGTTTCC
AACCGATTTTCTGGGGTCCCAGACAGGTTCAGTGGCAGTGGATCAGGGA
CAGATTTCACACTCAAGATCAGCAGAGTGGAGGCTGAGGATCTGGGAGT
TTATTTCTGCTCTCAAAGTACACATGTTCCGTACACTTTCGGAGGGGGG
ACCAAGCTGGAAATAAAACGGGCTGAT mAb 10C8 heavy chain sequence: 352 bp
(SEQ ID No. 15)
TGGGGCAGAGCTTGTGAGGTCAGGGGCCTCAGTCAAGTTGTCCTGCACA
TCTTCTGGCTTCAACATTAAAGACTACTTTCTACACTGGGTGAAACAGA
GGCCTGAACAGGGCCTGGAGTGGATTGGATGGATTGATCCTGAGAATGG
TGATACTGAATATGCCCCGAAGTTCCAGGACAAGGCCACTATGACTGCA
GACACATCCTCCAACACAGCCTACCTGCACCTCAGCAGCCTGACATCTG
AGGACACTGGCGTCTATTACTGTAATGCAGATGGTAACTACGGGAAGAA
CTACTGGGGCCAAGGCACCACTCTCACCGTCTCCTCAGCCAAAACAACA
GCCCCATCG mAb 10C8 light chain sequence: 324 bp
(SEQ ID No. 16)
CTCTCCCTGCCTGTCAGTCTTGGAGATCAAGCCTCCATCTCTTGCAGAT
CTAGTCAGAGCCTTGTACACAGTAATGGAAACACCTTTTTACATTGGTA
CCTGCAGAAGCCAGGCCAGTCTCCAAAGCTCCTGATCTACAGAGTTTCC
AACCGATTTTCTGGGGTCCCAGACAGGTTCAGTGGCAGTGGATCAGGGA -continued

CAGATTTCACACTCAAGATCAGCAGAGTGGAGGCTGAGGATCTGGGAGT

TTATTTCTGCTCTCAAAGTACACATGTTCCTCCGTACACGTTCGGAGGG

GGGACCAAGCTGGAAATAAAACGGGCTGAT

In another embodiment of the invention, one or more of the nucleic acid sequences described above encoding the antibody are subjected to humanization techniques or converted into chimeric human molecules for generating a variant antibody which has reduced immunogenicity in humans. Humanization techniques are well known in the art—see for example U.S. Pat. No. 6,309,636 and U.S. Pat. No. 6,407,213 which are incorporated herein by reference specifically for their disclosure on humanization techniques. Chimerics are also well known, see for example U.S. Pat. No. 6,461,824, U.S. Pat. No. 6,204,023, U.S. Pat. No. 6,020,153 and U.S. Pat. No. 6,120,767 which are similarly incorporated herein by reference.

In one embodiment of the invention, chimeric antibodies are prepared by preparing an expression vector which comprises a nucleic acid encoding a constant region domain of a human light or heavy chain genetically linked to a nucleic acid encoding a light chain variable region selected from the group consisting of 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14) and 10C8-light (SEQ ID No. 16) or a heavy chain variable region selected from the group consisting of 1H3-heavy (SEQ ID No. 1); 2G4-heavy (SEQ ID No. 3); 4G7-heavy (SEQ ID No. 5); 5D2-heavy (SEQ ID No. 7), 5E6-heavy (SEQ ID No. 9), 7C9-heavy (SEQ ID No. 11), 7G4-heavy (SEQ ID No. 13) and 10C8-heavy (SEQ ID No. 15). It is of note that all of these sequences are described above.

In another embodiment of the invention, there are provided recombinant antibodies comprising at least one modified variable region, said region selected from the group consisting of 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14), 10C8-light (SEQ ID No. 16), 1H3-heavy (SEQ ID No. 1); 2G4-heavy (SEQ ID No. 3); 4G7-heavy (SEQ ID No. 5); 5D2-heavy (SEQ ID No. 7), 5E6-heavy (SEQ ID No. 9), 7C9-heavy (SEQ ID No. 11), 7G4-heavy (SEQ ID No. 13) and 10C8-heavy (SEQ ID No. 15), in which at least one but fewer than about 30 of the amino acid residues of said variable region has been changed or deleted without disrupting antigen binding. It is of note that all of these sequences are described above.

In yet other embodiments, immunoreactive fragments of any of the above-described monoclonal antibodies, chimeric antibodies or humanized antibodies are prepared using means known in the art, for example, by preparing nested deletions using enzymatic degradation or convenient restriction enzymes.

It is of note that in all embodiments describing preparation of humanized antibodies, chimeric antibodies or immunoreactive fragments of monoclonal antibodies, these antibodies are screened to ensure that antigen binding has not been disrupted. This may be accomplished by any of a variety of means known in the art, but one convenient method would involve use of a phage display library. As will be appreciated by one of skill in the art, as used herein, 'immunoreactive fragment' refers in this context to an antibody fragment reduced in length compared to the wild-type or parent antibody which retains an acceptable degree or percentage of binding activity to the target antigen. As will be appreciated by one of skill in the art, what is an acceptable degree will depend on the intended use.

It is of note that as discussed herein, any of the above-described antibody or humanized variant thereof may be formulated into a pharmaceutical treatment for providing passive immunity for individuals suspected of or at risk of developing hemorrhagic fever comprising a therapeutically effective amount of said antibody. The pharmaceutical preparation may include a suitable excipient or carrier. See, for example, Remington: The Science and Practice of Pharmacy, 1995, Gennaro ed. As will be apparent to one knowledgeable in the art, the total dosage will vary according to the weight, health and circumstances of the individual as well as the efficacy of the antibody.

While the preferred embodiments of the invention have been described above, it will be recognized and understood that various modifications may be made therein, and the appended claims are intended to cover all such modifications which may fall within the spirit and scope of the invention.

TABLE 1

Dose-dependent protective efficacy of McAbs in mice

| Treatment[a] | Dose (μg/treatment) | Meantime to death[b] | No. of survivors/total |
|---|---|---|---|
| McAb 4G7 | 100 | 7.00 (n = 1) | 5/6 |
| | 50 | 7.00 (n = 1) | 5/6 |
| | 25 | 6.00 (n = 3) | 3/6 |
| | 12.5 | 6.80 (n = 5) | 1/6 |
| | 6.25 | 8.20 (n = 5) | 2/6 |
| McAb 5D2 | 100 | N/A[c] | 6/6 |
| | 50 | N/A[c] | 6/6 |
| | 25 | N/A[c] | 6/6 |
| | 12.5 | N/A[c] | 6/6 |
| | 6.25 | 7.50 (n = 2) | 4/6 |
| McAb 5E6 | 100 | N/A[c] | 6/6 |
| | 50 | N/A[c] | 6/6 |
| | 25 | N/A[c] | 6/6 |
| | 12.5 | 6.50 (n = 2) | 4/6 |
| | 6.25 | 6.67 (n = 3) | 3/6 |
| McAb 7C9 | 100 | N/A[c] | 6/6 |
| | 50 | N/A[c] | 6/6 |
| | 25 | 7.00 (n = 1) | 5/6 |
| | 12.5 | 7.00 (n = 1) | 5/6 |
| | 6.25 | 6.50 (n = 4) | 2/6 |
| McAb 7G4 | 100 | N/A[c] | 6/6 |
| | 50 | 7.50 (n = 1) | 4/6 |
| | 25 | 7.00 (n = 1) | 5/6 |
| | 12.5 | 7.60 (n = 5) | 1/6 |
| | 6.25 | 6.60 (n = 5) | 1/6 |
| McAb 10C8 | 100 | 7.00 (n = 1) | 5/6 |
| | 50 | 7.00 (n = 1) | 5/6 |
| | 25 | 7.50 (n = 4) | 2/6 |
| | 12.5 | 7.00 (n = 5) | 1/6 |
| | 6.25 | 6.40 (n = 5) | 1/6 |
| PBS | | 5.80 (n = 5) | 0/5 |

[a]Mice were intraperitoneally treated with antibodies 1 day after challenge with 1000 LD50 of the mouse-adapted Ebola virus.
[b]Data for animals that died (numbers of animals are shown in parentheses).
[c]N/A: not applicable.

TABLE 2

Time dependency of the protective efficacy of MAbs in mice

| MAbs | Day of treatment[a] | Mean time to death[b] | No. of survivors/total |
|---|---|---|---|
| 1H3 | −4 | 6.70 ± 0.61 (n = 10) | 0/10 |
| 100 μg | −1 | 6.60 ± 0.61 (n = 10) | 0/15 |
| | +1 | 8.10 ± 0.74 (n = 9) | 6/15 |

TABLE 2-continued Time dependency of the protective efficacy of MAbs in mice

| MAbs | Day of treatment[a] | Mean time to death[b] | No. of survivors/total |
|---|---|---|---|
|  | +2 | 6.60 ± 0.80 (n = 5) | 5/10 |
|  | +3 | 6.40 ± 0.97 (n = 10) | 0/10 |
| 2G4 | −4 | 7.40 ± 0.63 (n = 10) | 0/10 |
| 100 μg | −1 | 7.86 ± 0.74 (n = 14) | 1/15 |
|  | +1 | 8.00 (n = 6) | 9/15 |
|  | +2 | 7.30 ± 0.47 (n = 3) | 7/10 |
|  | +3 | 5.70 ± 1.13 (n = 10) | 0/10 |
| 4G7 | −4 | 7.42 ± 0.46 (n = 7) | 3/10 |
| 100 μg | −1 | 7.08 ± 0.74 (n = 14) | 1/15 |
|  | +1 | 8.25 ± 0.43 (n = 4) | 11/15 |
|  | +2 | n/a[c] | 10/10 |
|  | +3 | 5.67 ± 1.34 (n = 9) | 1/10 |
| 5D2 | −4 | 7.00 (n = 1) | 9/10 |
| 100 μg | −1 | 8.00 ± 1.00 (n = 2) | 13/15 |
|  | +1 | n/a | 15/15 |
|  | +2 | 7.00 (n = 4) | 6/10 |
|  | +3 | 6.30 ± 1.05 (n = 10) | 0/10 |
| 5E6 | −4 | 7.00 (n = 2) | 8/10 |
| 100 μg | −1 | 8.25 ± 0.43 (n = 4) | 11/15 |
|  | +1 | 7.00 (n = 1) | 14/15 |
|  | +2 | 6.00 (n = 1) | 9/10 |
|  | +3 | 5.80 ± 1.03 (n = 10) | 0/10 |
| 7C9 | −4 | 7.00 (n = 1) | 9/10 |
| 100 μg | −1 | 7.75 ± 0.43 (n = 4) | 11/15 |
|  | +1 | 8.00 ± 0.82 (n = 3) | 12/15 |
|  | +2 | 7.00 (n = 1) | 9/10 |
|  | +3 | 6.10 ± 0.67 (n = 10) | 0/10 |
| 7G4 | −4 | 8.20 ± 0.71 (n = 10) | 0/10 |
| 100 μg | −1 | 8.07 ± 0.59 (n = 14) | 1/15 |
|  | +1 | n/a | 15/15 |
|  | +2 | 7.10 ± 0.57 (n = 9) | 1/10 |
|  | +3 | 6.70 ± 0.44 (n = 10) | 0/10 |
| 10C8 | −4 | 7.83 ± 0.64 (n = 6) | 4/10 |
| 100 μg | −1 | 7.64 ± 1.17 (n = 14) | 1/15 |
|  | +1 | 8.50 ± 0.50 (n = 2) | 13/15 |
|  | +2 | 6.83 ± 0.37 (n = 6) | 4/10 |
|  | +3 | 6.30 ± 1.13 (n = 10) | 0/10 |
| 17F8[d] | −4 | 6.00 ± 1.10 (n = 9) | 1/10 |
| 100 μg | −1 | 6.13 ± 0.88 (n = 15) | 0/15 |
|  | +1 | 7.21 ± 0.86 (n = 14) | 1/15 |
|  | +2 | 6.10 ± 0.83 (n = 10) | 0/10 |
|  | +3 | 6.00 ± 1.13 (n = 10) | 0/10 |
| PBS | −4 | 5.40 ± 1.43 (n = 10) | 0/10 |
|  | −1 | 6.60 ± 0.80 (n = 5) | 0/5 |
|  | +3 | 5.00 ± 0.60 (n = 10) | 0/10 |

[a]Mice were intraperitoneally treated with each MAb at indicated time before or after challenge with 1000 LD50 of the mouse-adapted Ebola virus.
[b]Data for animals that died (numbers of animals are shown in parentheses).
[c]N/A: not applicable.
[d]Control Mab: anti-MAR GP.

TABLE 3

Protective efficacy of MAbs in guinea pigs

| Treatment | Day of treatment[a] | Meantime to death[b] | No. of survival/Tatal[c] |
|---|---|---|---|
| Cocktail of |  |  |  |
| 5D2(3 mg) + | 1 |  |  |
| 4G7(2 mg) + 1H3(1 mg) + | 2 | N/A[d] | 6/6 |
| 2G4(1 mg) |  |  |  |
| Cocktail of |  |  |  |
| 5E6(3 mg) + | 1 |  |  |
| 4G7(2 mg) + 1H3(1 mg) + | 2 | N/A | 6/6 |
| 2G4(1 mg) |  |  |  |
| Cocktail of |  |  |  |
| 7C9(3 mg) + | 1 |  |  |
| 4G7(2 mg) + 1H3(1 mg) + | 2 | N/A | 6/6 |
| 2G4(1 mg) |  |  |  |
| Cocktail of |  |  |  |
| 7G4(3 mg) + | 1 |  |  |
| 4G7(2 mg) + 1H3(1 mg) + | 2 | N/A | 6/6 |
| 2G4(1 mg) |  |  |  |
| Cocktail of |  |  |  |
| 10C8(3 mg) + | 1 |  |  |
| 4G7(2 mg) + 1H3(1 mg) + | 2 | 9.00(n = 1) | 5/6 |
| 2G4(1 mg) |  |  |  |
| Cocktail of |  |  |  |
| PBS + | 1 |  |  |
| PBS | 2 | 7.00(n = 6) | 0/6 |

[a]Guinea pigs were intraperitoneally treated with the MAbs as showed dose in the table on the indicated days after challenge with 1000 LD50 of the guinea pig-adapted Ebola virus.
[b]Data for all animals that died(numbers of animals are shown in parentheses).
[c]Survival rate on day 28 after challenge.
[d]N/A: not applicable.

TABLE 4

Summary of ELISA Result of Anti-Ebola-GP McAbs

| McAB | Isotype | eVLPs | eGP1,2 ΔTm | sGP 1-295aa | Rf-GP1 sub-f-D 157-369aa | Mucin domain 333-458aa | GP1 1-501aa |
|---|---|---|---|---|---|---|---|
| 1H3 | IgG2a,κ | + | + | + | − | − | + |
| 2G4 | IgG2b,κ | + | + | − | − | − | + |
| 4G7 | IgG2a,κ | + | + | − | − | − | + |
| 5D2 | IgG2a,κ | + | + | − | + | + | + |
| 5E6 | IgG2a,λ | + | + | − | + | + | + |
| 7C9 | IgG2a,κ | + | + | − | +/− | + | + |
| 7G4 | IgG1,κ | + | + | − | − | +/− | + |
| 10C8 | IgG2a,κ | + | + | − | − | +/− | + |

Antigens (0.3 μg/well) were coated in 96 well microtitre plate then blocking with 2% skim milk. Serial dilutions of each MAb were applied to the plate followed by HRP-conjugated goat anti-mouse IgG. After incubabing with substrate, the asorbance awas read at OD405. Cut off was 2X background.

TABLE 5

Prolonged survival seen in McAb-treated Guinea pigs

| Treatment[a] | Mean time to death[b] | Student's t-test |
|---|---|---|
| MAb 1H3 | 11.7 ± 2.18 (n = 5) | p = 0.0181 |
| MAb 2G4 | 11.5 ± 1.50 (n = 2) | N/A[c] |
| MAb 4G7 | 10.5 ± 1.50 (n = 2) | N/A[c] |
| MAb 5D2 | 9.4 ± 1.02 (n = 5) | p = 0.0244 |
| MAb 5E6 | 10.8 ± 1.47 (n = 5) | p = 0.0092 |
| MAb 7C9 | 9.6 ± 0.80 (n = 5) | p = 0.0056 |
| MAb 7G4 | 9.6 ± 0.80 (n = 5) | p = 0.0056 |
| MAb 10C8 | 9.4 ± 1.20 (n = 5) | p = 0.0428 |
| PBS | 7.67 ± 0.75 (n = 6) | N/A[c] |

[a]Guinea pigs were intraperitoneally treated with 5 mg of the MAb as showed in the table on day 1 after challenge with 1000 LD50 of the guinea pig-adapted Ebola virus.
[b]Data for all animals that died (numbers of animals are shown in parentheses).
[c]N/A: not applicable.

TABLE 6

Protective efficacy of MAbs in guinea pigs

| Treatment | Day of treatment[a] | Meantime to death[b] | No. of survival/Tatal[c] |
|---|---|---|---|
| Cocktail of 4G7(2 mg) + 1H3(1.5 mg) + 2G4(1.5 mg) | −1 | 11.17 ± 3.09 (n = 3) | 3/6 |
| Cocktail of 4G7(2 mg) + 1H3(1.5 mg) + 2G4(1.5 mg) | +1 | 7.92 ± 0.42 (n = 3) | 3/6 |
| Cocktail of 4G7(2 mg) + 1H3(1.5 mg) + 2G4(1.5 mg) | +2 | N/A[d] | 6/6 |
| Cocktail of 4G7(2 mg) + 1H3(1.5 mg) + 2G4(1.5 mg) | +3 | 11.17 ± 3.09 (n = 3) | 4/6 |
| PBS | +2 | 6.58 ± 0.59 (n = 6) | 3/6 |

[a]Guinea pigs were intraperitoneally treated with the MAbs as showed dose in the table on the indicated days before or after challenge with 1000 LD50 of the guinea pig-adapted Ebola virus.
[b]Data for all animals that died(numbers of animals are shown in parentheses).
[c]Survival rate on day 28 after challenge.
[d]N/A: not applicable.

TABLE 7

Epitopes bound by ZEbov GP McAbs

| mAb name | Ebola GPs with epitope | epitope sequence | epitope position |
|---|---|---|---|
| 1H3(IgG2a/κ): | sGP[a] | SNTTGKLIWKVNPEI (SEQ ID NO: 17) | 267-280aa |
| 2G4(IgG2b/κ): | GP2[a] | REAIVNAQPKCNPNL (SEQ ID NO: 18) | 502-516aa |
| 4G7(IgG2a/κ): | GP2[a] | REAIVNAQPKCNPNL (SEQ ID NO: 19) | 502-516aa |
| 5D2 (IgG2a/κ): | GP1[b,c,d] | DPGTNTTTEDHKIMA (SEQ ID NO: 20) | 329-343aa |
| 5E6 (IgG2a/λ): | GP1[b,c,d] | ATQVEQHHRRTDNDS (SEQ ID NO: 21) | 401-415aa |
| 7C9(IgG2a,κ): | GP1[b,c] | unknown | unknown |
| 7G4(IgG1, κ): | GP1[b,c] | unknown | unknown |
| 10C8(IgG2a,κ): | GP1[b,c] | unknown | unknown |

[a]determined by using recombinant vesicular stamatitis virus(VSV) containing ZEbov GP gene to identify the amino acid changes in antigenic variants that escape antibody neutralization;
[b]determined by Western blot reactivity with Ebola Zaire 1976 or VLPs,
[c]determined by ELISA using recombinant GP1 protein;
[d]determined by ELISA using peptide library.

The invention claimed is:

1. A monoclonal antibody that binds Ebola glycoprotein comprising a light chain variable region comprising the amino acid sequence deduced from the nucleic acid molecule as set forth in SEQ ID NO: 6 and a heavy chain variable region comprising the amino acid sequence deduced from the nucleic acid molecule as set forth in SEQ ID NO:5.

2. A method of preparing a chimeric antibody that binds Ebola glycoprotein comprising:
   providing an expression vector comprising a nucleic acid molecule encoding a constant region domain of a human light chain genetically linked to a nucleic acid molecule encoding a light chain variable region comprising the nucleic acid molecule as set forth in SEQ ID No: 6; and
   providing an expression vector comprising a nucleic acid molecule encoding a constant region domain of a human heavy chain genetically linked to a nucleic acid molecule encoding a heavy chain variable region comprising the amino acid sequence deduced from the nucleic acid molecule as set forth in SEQ ID No. 5;
   expressing the expression vectors in a suitable host; and
   recovering the chimeric antibody that binds Ebola glycoprotein from said host.

3. A method of preparing a chimeric antibody that binds Ebola glycoprotein comprising:
   providing an expression vector comprising a nucleic acid molecule encoding a constant region domain of a human light chain genetically linked to a nucleic acid molecule encoding a light chain variable region comprising the nucleic acid molecule as set forth in SEQ ID No: 6; and a nucleic acid molecule encoding a constant region domain of a human heavy chain genetically linked to a nucleic acid molecule encoding a heavy chain variable region comprising the amino acid sequence deduced from the nucleic acid molecule as set forth in SEQ ID No. 5;
   expressing the expression vector in a suitable host; and
   recovering the chimeric antibody that binds Ebola glycoprotein from said host.

4. A pharmaceutical composition comprising the monoclonal antibody of claim 1 and a pharmaceutically acceptable excipient or carrier.

* * * * *